United States Patent [19]
Greene

[11] 4,042,599
[45] Aug. 16, 1977

[54] PROCESS FOR PRODUCING 2-PYRROLIDONE

[75] Inventor: Janice L. Greene, Chagrin Falls, Ohio

[73] Assignee: The Standard Oil Company, Cleveland, Ohio

[21] Appl. No.: 591,882

[22] Filed: June 30, 1975

[51] Int. Cl.$^2$ .......................................... C07D 207/26
[52] U.S. Cl. ......................................... 260/326.5 FN
[58] Field of Search ............................. 260/326.5 FN

[56] References Cited

U.S. PATENT DOCUMENTS

| 2,351,939 | 6/1974 | Drossbach et al. | 260/326.5 FN |
|---|---|---|---|
| 3,095,423 | 6/1963 | Copenhaver et al. | 260/326.5 FN |
| 3,644,402 | 2/1972 | Takagi et al. | 260/326.5 FN |
| 3,781,402 | 12/1973 | Davis | 260/326.5 FN |

FOREIGN PATENT DOCUMENTS 856,822  12/1960  United Kingdom ....... 260/326.5 FN

Primary Examiner—Donald G. Daus
Assistant Examiner—Mary C. Vaughn
Attorney, Agent, or Firm—Herbert D. Knudsen; Evelyn R. Kosman

[57] ABSTRACT

A process for producing 2-pyrrolidone by the simultaneous hydrolysis and hydrogenation of succinonitrile at elevated temperatures and at hydrogen pressures below 500 psi in the presence of a hydrogenation catalyst.

3 Claims, No Drawings

PROCESS FOR PRODUCING 2-PYRROLIDONE

This invention relates to an improved process for the synthesis of 2-pyrrolidone (also known as 2-pyrrolidinone) from succinonitrile. More particularly, this invention relates to the synthesis of 2-pyrrolidone by the simultaneous hydrolysis and hydrogenation of succinonitrile in the presence of a hydrogenation catalyst at hydrogen pressures of less than 500 psi.

BACKGROUND OF THE INVENTION

Pyrrolidone is particularly useful as an intermediate in the preparation of Nylon-4, in the preparation of N-methyl pyrrolidone and N-vinyl pyrrolidone which are useful as organic solvents, and in the formation of polymers which have certain specific properties. Heretofore, pyrrolidone has been prepared from succinonitrile by various processes utilizing high pressures of hydrogen. For example, according to U.S. Pat. No. 3,095,423 2-pyrrolidone is prepared in a liquid phase process comprising the simultaneous hydrogenation and hydrolysis of succinonitrile utilizing aqueous ammonia and hydrogen pressures of at least 500 psi, and preferably hydrogen pressures of from 1000–2000 psi. U.S. Pat. No. 3,781,298 also describes a single step process for preparing 2-pyrrolidone by hydrogenating succinonitrile in an aqueous solution but at pressures greater than 2000 psig. U.S. Pat. No. 3,644,402 discloses a two-step process for hydrolyzing and hydrogenating succinonitrile sequentially, wherein the hydrolysis reaction is conducted in aqueous ammonia and the hydrogenation in the presence of a nitrogen-containing basic organic solvent at pressures of from about 750 to 3000 psi. None of the processes of the prior art, however, teach that considerable improvement in the yields of pyrrolidone can be obtained by the process of the instant invention utilizing hydrogen pressures below 500 psi.

SUMMARY OF THE INVENTION

According to the present invention, it has been discovered that improved yields of pyrrolidone can be obtained by contacting an aqueous mixture of succinonitrile with hydrogen at an elevated temperature in the presence of a hydrogenation catalyst, the improvement comprising conducting the reaction at hydrogen pressures of from 100 up to 500 psi. The overall reaction taking place in this process may be represented by the following equation:

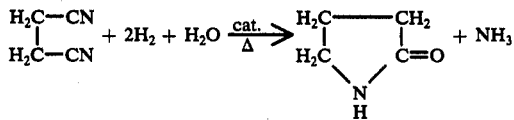

It is surprising that maximum conversions and yields of 2-pyrrolidone are obtained in this process using hydrogen pressures below 500 psi, particularly in view of the disclosure in U.S. Pat. No. 3,095,423 wherein it is stated that at pressures lower than 500 psi., the rate of conversion becomes too slow for economic consideration. The use of lower hydrogen pressures as employed in the instant process minimizes the excessive hydrogenation of succinonitrile to pyrrolidine and related products, and it has the important economic significance in the need for less expensive reactor equipment.

Although this process can be successfully conducted at hydrogen pressures in the range of from 100 up to 500 psi, hydrogen pressures in the range of from about 300 to 490 psi are preferred.

The catalyst employed in this process may be any hydrogenation catalysts suitable for this process. Preferred catalysts are chosen from the group of hydrogenation catalysts containing the elements of nickel, chromium, platinum, palladium, rhodium, ruthenium, cobalt, copper and rhenium. Catalysts may take any form. For example, the catalysts may be the oxides, metals or Raney catalysts. They may be supported catalysts wherein the supporting medium may be carbon, alumina, silica, silica-alumina, titania, zirconia, kieselguhr or other well-known inert supports. The amount of the hydrogenation catalyst used may vary widely, and normally from about 0.1 to 40 percent by weight is used, based on the weight of succinonitrile employed in the reaction. However, it is more preferable to employ from about 3.5 to 35 weight percent catalyst based on the weight of the succinonitrile employed. The catalyst may be recovered from the reaction mixture by filtration or decantation and can be used repeatedly, normally without regeneration.

The ratio of the reactants-succinonitrile, water and hydrogen-charged to the reactor in this process are not critical. Water can be present in stoichiometric amounts, i.e., one mole of water/mole of succinonitrile, or excess water may be used. Generally, it is preferred to employ from about 5–25 moles of water per mole of succinonitrile. The desirable upper limit of the amount of water used is governed by the excessive hydrolysis of succinonitrile to succinimide and by the economics of product recovery, and the lower limit is governed by polymer formation. Optionally, minor amounts of various reaction promoters may be advantageously incorporated into the reaction mixture during the course of the reaction, and such promoters as 2-pyrrolidone and the N-alkyl-2-pyrrolidones wherein the alkyl group may contain from 1 to 6 carbon atoms are contemplated to be within the scope of the invention. When utilized, beneficial results are readily obtained with these reaction promoters employed in concentrations ranging from about 0.1 to 1.5 moles per mole of succinonitrile.

The reaction may be conducted by means of various techniques using various reactors, and both batch-type and continuous operations are contemplated. Additional beneficial results are obtained by recycling the reaction product to the reaction mixture. In a preferred practice, water, succinonitrile, catalyst and optionally a promoter are charged to a reactor in the desired concentrations, and the reactor is then closed and further charged with hydrogen to the desired pressure. The temperature of the reaction mixture is then raised to the level desired, with stirring. The reaction temperature may range from about 50° to 300° C but preferably temperatures within the range of from about 100° to 200° C are employed. The reaction is continued at the desired temperature for a period of time ranging from about 0.5 to 6 hours, however, with continuous operation contact times may be as low as 0.1 hours. Preferably the reaction time is within the range of from about 2 to 5 hours, after which time the heat is removed, and the reaction mass is allowed to cool. The reaction mixture is then filtered to remove the catalyst and flash distilled to remove excess water and volatile components. The product, 2-pyrrolidone, is then recovered in good yields by fractional distillation of the remaining reaction mixture.

SPECIFIC EMBODIMENTS

Comparative Examples A–E

The reactions in comparative examples A–E which are not representative of the present invention were carried out by placing deionized water, succinonitrile and a hydrogenation catalyst in a one-liter, stainless steel Parr autoclave. In comparative examples B–E, a reaction promoter was added to the reaction mixture in the concentrations indicated. The autoclave was flushed with nitrogen for 5 minutes, and with stirring was pressured to 200 psig. with nitrogen and checked for leakage by increasing the nitrogen pressure to twice that of the working pressure for a period of 15 minutes. When no leaks were detected the nitrogen was vented, the autoclave heated to 60° C for ½ hour, then pressured with hydrogen to the working pressure. As hydrogen was consumed, hydrogen was added from time to time to maintain the working pressure. Stirring and heating were continued for about one hour after the hydrogen addition and before the reaction temperature of 140° C was reached. The exothermic reaction carried the reaction to a slightly higher temperature as indicated in Table 1. Periodically, samples were removed from the autoclave and were analyzed by gas-liquid chromatography for unreacted succinonitrile, pyrrolidone and the hydrolysis products, succinimide and succinic acid. The condition under which the maximum pyrrolidone conversion was observed was then recorded. At that time the succinonitrile conversion was usually complete. Other by-products identified in addition to succinimide and succinic acid were pyrrolidine and butyrolactone. The reaction contents were then cooled, filtered, and concentrated by vacuum stripping.

EXAMPLES 1–4

The experimental procedure employed in Examples A–E was repeated in Examples 1–4 which represent the invention, with the exception that the hydrogen pressure was varied as indicated and no reaction promoter was employed in Example 1.

The examples in Table 1 illustrate that in accordance with the present invention, improved yields of 2-pyrrolidone are obtained at hydrogen pressures below 500 psi, and that maximum yields are obtained with hydrogen pressures of about 465 psi. The improved yield at the lower hydrogen pressures is also illustrated in reactions utilizing hydrogenation catalysts of various composition and in the reactions utilizing reaction promoters.

Table 1
Effect of Hydrogen Pressure on the Conversion of Succinonitrile to 2-Pyrrolidone

| Example ([1]) | | Catalyst | Grams Catalyst/ Mole SN | Promoter, | Moles/ Mole SN | Reaction Conditions | | | Net Mole % Conversion to Pyrrolidone |
|---|---|---|---|---|---|---|---|---|---|
| | | | | | | $H_2$Press. Psi | Temp. °C | Time, Hours | |
| Comp. | A | Raney Nickel | 25 | — | — | 1015 | 142 | 3.75 | 19.5 |
| | 1 | Raney Nickel | 25 | — | — | 465 | 145 | 4.0 | 31.0 |
| Comp. | B | Nickel Boride | 3 | 2-Pyrrolidone | 0.5 | 515 | 143 | 4.0 | 44.3 |
| Comp. | C | Nickel Boride | 3 | 2-Pyrrolidone | 0.5 | 665 | 136 | 4.5 | 41.6 |
| Comp. | D | Nickel Boride | 3 | 2-Pyrrolidone | 0.5 | 765 | 140 | 3.2 | 38.0 |
| | 2 | Nickel Boride | 3 | 2-Pyrrolidone | 0.5 | 365 | 135 | 3.0 | 38.2 |
| | 3 | Nickel Boride | 3 | 2-Pyrrolidone | 0.5 | 465 | 144 | 4.9 | 54.9 |
| Comp. | E | Raney Nickel | 25 | N-Methyl Pyrrolidone | 0.4 | 1015 | 145 | 4.0 | 23.7 |
| | 4 | Raney Nickel | 25 | N-Methyl Pyrrolidone | 0.4 | 465 | 141 | 2.0 | 44 |

([1])Moles of water/mole of succinonitrile = 20

I claim:

1. In the process for the preparation of 2-pyrrolidone by contacting an aqueous mixture of succinonitrile with hydrogen at an elevated temperature in the presence of a hydrogenation catalyst, the improvement comprising conducting the reaction at a hydrogen pressure within the range of from 300 to 490 psi.

2. The process in claim 1 wherein the reaction temperature is in the range of from 50° to 300° C.

3. The process in claim 2 wherein the hydrogenation catalyst is a nickel-containing catalyst.

* * * * *